(12) United States Patent
Pham

(10) Patent No.: US 11,918,135 B2
(45) Date of Patent: *Mar. 5, 2024

(54) BODY-MOUNTABLE CUSHION STRUCTURE FOR POST- SURGICAL SUPPORT AND PROTECTION AND METHOD OF USE

(71) Applicant: Maelee Pham, Greenwood, IN (US)

(72) Inventor: Maelee Pham, Greenwood, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/953,686

(22) Filed: Sep. 27, 2022

(65) Prior Publication Data

US 2023/0225527 A1 Jul. 20, 2023

Related U.S. Application Data

(63) Continuation of application No. 16/221,542, filed on Dec. 16, 2018, now Pat. No. 11,452,391.

(60) Provisional application No. 62/599,687, filed on Dec. 16, 2017.

(51) Int. Cl.
*A47G 9/10* (2006.01)
*A41D 13/05* (2006.01)
*A41D 13/12* (2006.01)
*A61F 5/03* (2006.01)
*A61F 7/02* (2006.01)

(52) U.S. Cl.
CPC ....... *A47G 9/1036* (2013.01); *A41D 13/0518* (2013.01); *A41D 13/1236* (2013.01); *A47G 9/1045* (2013.01); *A61F 5/03* (2013.01); *A61F 2007/023* (2013.01)

(58) Field of Classification Search
CPC ................ A47G 9/1036; A47G 9/1045; A41D 13/0518; B63C 9/13; B60R 21/055; A61F 2007/023
See application file for complete search history.

(56) References Cited

U.S. PATENT DOCUMENTS

| | | | |
|---|---|---|---|
| 1,618,347 | A | 2/1927 | McSherry |
| 1,843,617 | A | 2/1932 | Marshall |
| 2,042,152 | A | 5/1936 | Howland |
| 2,056,767 | A | 10/1936 | Blath |
| 2,265,690 | A | 12/1941 | Fiedler |
| 3,065,476 | A | 11/1962 | Brown |
| 3,550,159 | A | 12/1970 | Alarco |
| 4,884,295 | A | 12/1989 | Cox |

(Continued)

*Primary Examiner* — Eric J Kurilla
(74) *Attorney, Agent, or Firm* — Reichel Stohry Dean LLP; Mark C. Reichel; Natalie J. Dean

(57) ABSTRACT

Pivotably connected upper and lower cushions may be sized and shaped to protect chest and lower abdomen areas of a patient, respectively. The cushion structure may be held against the chest and/or abdomen areas of a patient by a combination of an adjustable and disconnectable neck strap attached to an upper portion of the upper cushion, and an adjustable length and resilient strap, such as an elastic belt binder, which may be positioned around the user's waist and the upper cushion. The lower cushion may pivotably move with the patient's legs, allowing the cushion structure to be comfortably used when moving between standing and seated positions, and providing improved protection from automotive seat belts. Pockets may be provided for positioning ice packs proximate the patient's body and for inconspicuously placing a negative-pressure wound therapy vacuum pump or other items.

19 Claims, 5 Drawing Sheets

(56) References Cited

U.S. PATENT DOCUMENTS

| | | |
|---|---|---|
| 5,075,897 A | 12/1991 | Daniels |
| 5,199,124 A | 4/1993 | Klemis |
| 5,261,420 A | 11/1993 | Grillo |
| 5,692,246 A | 12/1997 | Benedick |
| 5,996,118 A | 12/1999 | Carlone |
| 6,708,354 B1 | 3/2004 | Carter et al. |
| 8,578,526 B1 | 11/2013 | Rosso |
| 11,452,391 B2 * | 9/2022 | Pham ................. A41D 13/1236 |
| 2003/0052528 A1 | 3/2003 | Huggins |
| 2004/0238583 A1 | 12/2004 | Gordon |
| 2005/0120482 A1 | 6/2005 | Robie |
| 2005/0273935 A1 | 12/2005 | Cordova et al. |
| 2010/0170029 A1 | 7/2010 | Kordecki |
| 2013/0312192 A1 | 11/2013 | Lee |
| 2016/0128500 A1 | 5/2016 | Yuyungyuen |
| 2018/0281910 A1 | 10/2018 | Drohan |
| 2018/0292177 A1 | 10/2018 | Roby et al. |
| 2019/0069686 A1 | 3/2019 | Miller |
| 2019/0246819 A1 | 8/2019 | Lemoine et al. |
| 2020/0107658 A1 | 4/2020 | Emoff |
| 2020/0220248 A1 | 7/2020 | Verlinden et al. |
| 2020/0405064 A1 | 12/2020 | Jones |

\* cited by examiner

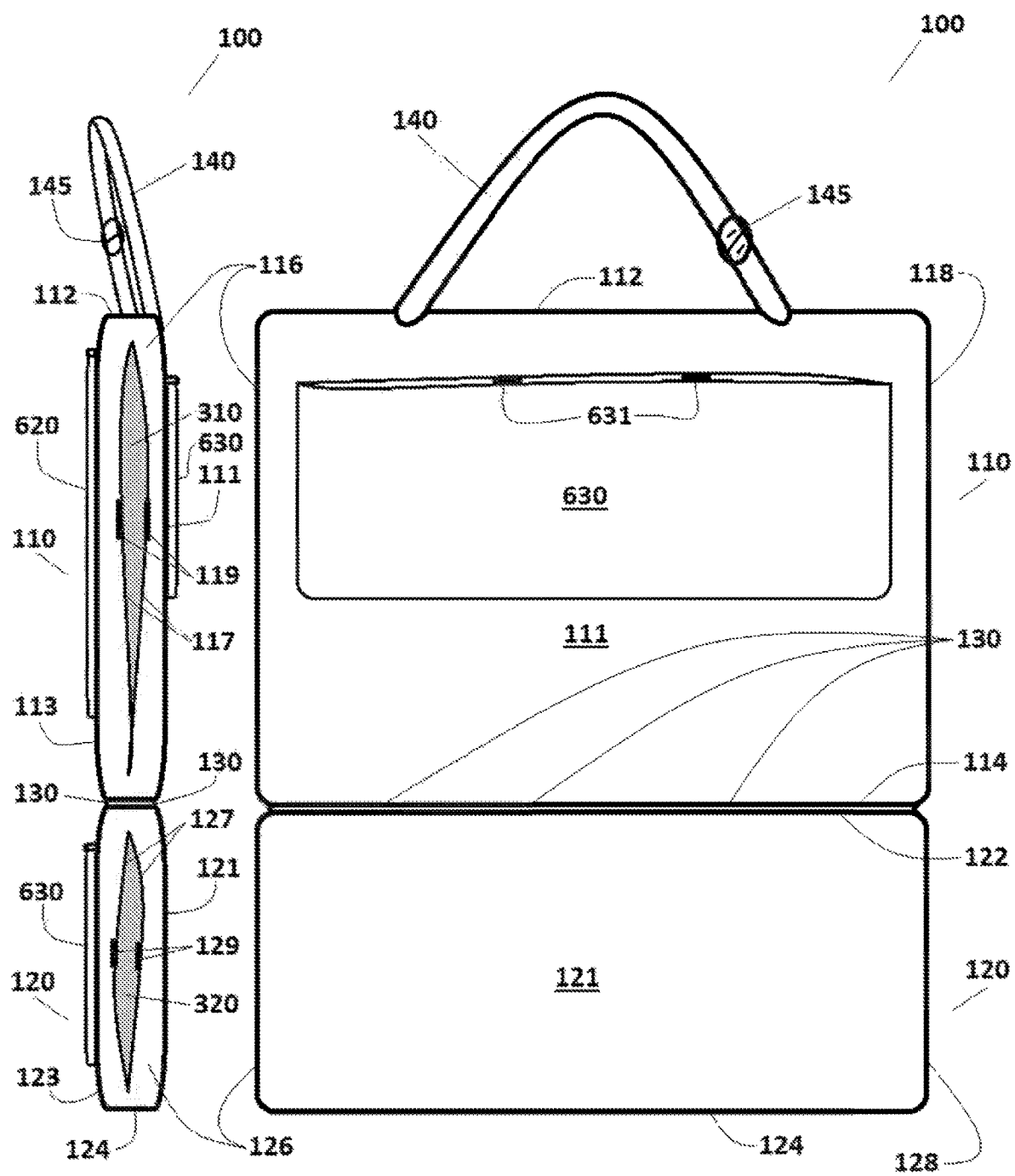

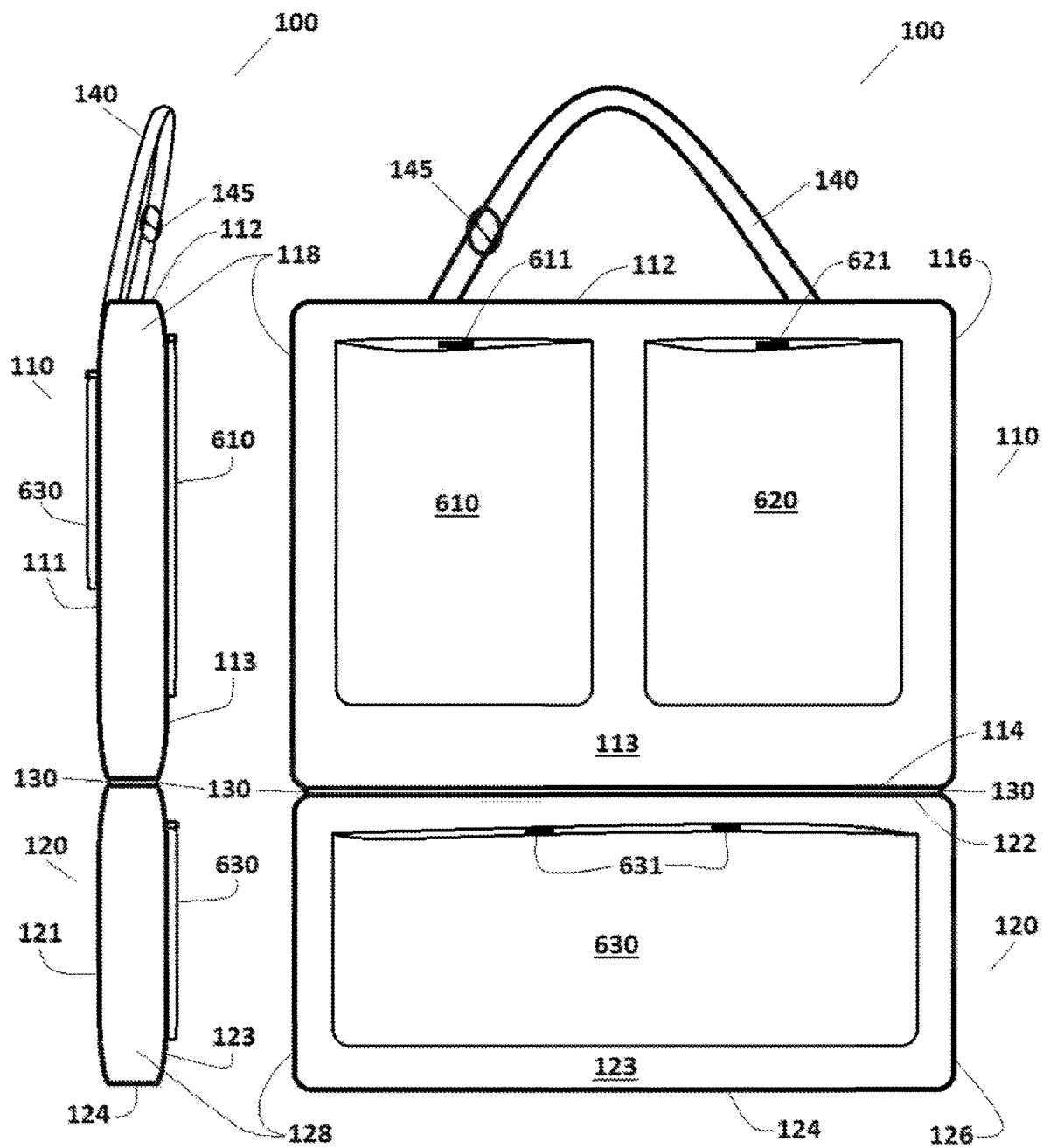

BODY-MOUNTABLE CUSHION STRUCTURE FOR POST-SURGICAL SUPPORT AND PROTECTION AND METHOD OF USE

PRIORITY

This application is related to, claims the priority benefit of, incorporates herein by reference in its entirety, and is a U.S. continuation patent application of, U.S. patent application Ser. No. 16/221,542, filed Dec. 16, 2018 and issued as U.S. Pat. No. 11,452,391 on Sep. 27, 2022, which is related to, and claims the priority benefit of, and incorporates herein by reference in its entirety, U.S. Provisional Patent Application Ser. No. 62/599,687, filed Dec. 16, 2017.

TECHNICAL FIELD

The present disclosure relates generally to a body-mountable cushion structure for post-surgical support and protection, and related methods of use.

BACKGROUND

Travel pillows and the like are known for providing cushioning between an automotive seatbelt and a user's body. For example, incorporated herein by reference is United States Patent Application Publication US 2003/0052528 A1 to Huggins, entitled Detachable Protective Pad for Abdominal Area, published Mar. 20, 2003 ("Huggins"). Also provided in the art is a chest pad for protecting a post-chest-surgery patient from an automotive seatbelt. Incorporated herein by reference is U.S. Pat. No. 5,692,246 to Benedick, entitled Chest Pillow Chest Protector, issued Dec. 2, 1997 ("Benedick"). However, none of the art of which Applicant is aware suitably addresses the support, comfort, therapeutic, and protection needs of many post-surgical patients, especially those having abdominal surgeries.

BRIEF SUMMARY

The present invention(s) elegantly overcome many of the drawbacks of prior systems and provide numerous additional improvements and benefits as will be apparent to persons of skill in the art. Included in certain example embodiments is an elongated planar resilient cushion structure that may be adapted to support and provide protection for any or all of a user's chest, abdomen, and torso, from automotive seat belts and the like. The cushion structure may be provided with one or more pockets on either or both sides of the cushion structure for removably containing one or more ice packs or other items for therapeutic treatment of the user, as well as other features.

For example, provided in various example embodiments is a cushion structure for a post-surgical patient to wear, comprising: an upper pillow portion, comprising: a first flexible and resilient cushion having a first thickness, a first width, and a first height, the first width and first height being perpendicular to the first thickness and to each other, the first width and first height approximating upper body width and rib cage height dimensions of a patient; a first fabric cover portion at least substantially surrounding and enclosing the first flexible and resilient cushion; a lower pillow portion, comprising: a second flexible and resilient cushion having a second thickness, a second width, and a second height, the second width and second height being perpendicular to the second thickness and to each other, the second width being at least approximately the same as the first width and the second height being less than the first height; a second fabric cover portion at least substantially surrounding and enclosing the second flexible and resilient cushion; an upper part of the lower pillow portion flexibly connected with a lower part of the upper pillow portion so the lower pillow portion can readily pivot with respect to the upper pillow portion; and one or more straps configured to engage the upper pillow portion and an upper body area of the patient to removably hold the upper pillow portion of the cushion structure proximate a chest area of the patient. 100071 in various example embodiments the cushion structure may further comprise a patient-facing first side and a second side opposite the first side, the upper pillow portion comprising one or more first pockets located on the upper pillow portion on the patient-facing first side, each of the one or more first pockets oriented and configured to removably receive therein an ice pack and to position the ice pack proximate a body area of the patient when the cushion structure is worn by the patient. One or more ice packs may be provided within one or more of the first pockets.

In various example embodiments the cushion structure may further comprise the lower pillow portion comprising one or more second pockets located on the lower pillow portion on the patient-facing first side, or on the second side opposite the patient-facing first side, or both, at least one of the one or more second pockets oriented and configured to removably and inconspicuously receive therein a negative-pressure wound therapy vacuum pump.

In various example embodiments the cushion structure may further comprise the first fabric cover portion comprising a first selectably openable access area located and sized so that the first flexible and resilient cushion can be removed and replaced through a first selectably openable access area. In various example embodiments the cushion structure may further comprise the second fabric cover portion comprising a second selectably openable access area located and sized so that the second flexible and resilient cushion can be removed and replaced through the second selectably openable access area.

In various example embodiments the cushion structure may further comprise the one or more straps comprising a first adjustable length strap attached at first end to a first location on an upper part of the upper pillow portion and attached at a second end to a second location on the upper part of the upper pillow portion, the first adjustable length strap configured to extend around, and be supported at least in part by, a neck area of the patient when the cushion structure is worn by the patient. In various example embodiments the cushion structure may further comprise the one or more straps comprising a second adjustable length strap configured to extend around, and be supported at least in part by, the upper pillow portion and a back area of the patient when the cushion structure is worn by the patient. In various example embodiments the second adjustable length strap may or may not be attached to the upper pillow portion.

Also provided in various example embodiments is a method of using a cushion structure, comprising the steps of: providing a cushion structure as described herein for a post-surgical patient to wear, and removably engaging the upper pillow portion with an upper body area of the patient with the one or more straps so that the upper pillow portion is proximate a chest area of the patient.

In various example embodiments the method of using a cushion structure may further comprise the steps of removably engaging the upper pillow portion with an upper body area of the patient with the one or more straps so that the lower pillow portion is proximate either a lower abdomen area of the patient, or an upper leg area of the patient, or both, when the upper pillow portion is proximate a chest area of the patient.

In various example embodiments the method of using a cushion structure may further comprise the steps of the patient moving between a standing position and a sitting position and moving an upper leg area of the patient relative to the chest area of the patient, the movement of the upper leg area of the patient causing the lower pillow portion to pivot with respect to the upper pillow portion. In various example embodiments the steps of moving an upper leg area of the patient relative to the chest area of the patient and causing the lower pillow portion to pivot with respect to the upper pillow portion, may further comprise the steps of: the patient moving between a first position outside of a vehicle and a second position seated inside a vehicle while wearing a vehicle seatbelt over the cushion structure.

Further provided in various example embodiments is a method of using a cushion structure, comprising the steps of: providing a cushion structure as described herein for a post-surgical patient to wear; placing at least one ice pack in the one or more first pockets; removably engaging the upper pillow portion with an upper body area of the patient with the one or more straps so that the upper pillow portion is proximate a chest area of the patient, the one or more ice packs are proximate a body area of the patient, and the lower pillow portion is proximate either a lower abdomen area of the patient, or an upper leg area of the patient, or both; the patient moving between a standing position and a sitting position and moving an upper leg area of the patient relative to the chest area of the patient, the movement of the upper leg area of the patient causing the lower pillow portion to pivot with respect to the upper pillow portion; and the patient moving between a first position outside of a vehicle and a second position seated inside a vehicle while wearing a vehicle seatbelt over the cushion structure.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

Various example embodiments are depicted in the accompanying drawings for illustrative purposes, and should in no way be interpreted as limiting the scope of the embodiments. Furthermore, various features of different disclosed embodiments can be combined to form additional embodiments, which are also part of this disclosure. It will be understood that certain components and details may not appear in the Figure(s) to assist in more clearly describing the invention. Additionally, it will be appreciated that the drawings may be not to scale and that portions of certain features or elements may be exaggerated for purpose of clarity and ease of understanding.

FIG. 3 is a left side elevation view of an example body-mountable cushion structure for post-surgical support and protection according to various example embodiments, shown with side openings partially open to reveal cushioning pads therein.

FIG. 4 is a front side elevation view of the example body-mountable cushion structure for post-surgical support and protection of FIG. 3, shown optionally without pockets on the front side.

FIG. 5 is a right side elevation view of the example body-mountable cushion structure for post-surgical support and protection of FIG. 3.

FIG. 6 is a rear side elevation view of the example body-mountable cushion structure for post-surgical support and protection of FIG. 3, shown optionally with example pockets on the rear side.

DETAILED DESCRIPTION

Figure 1:
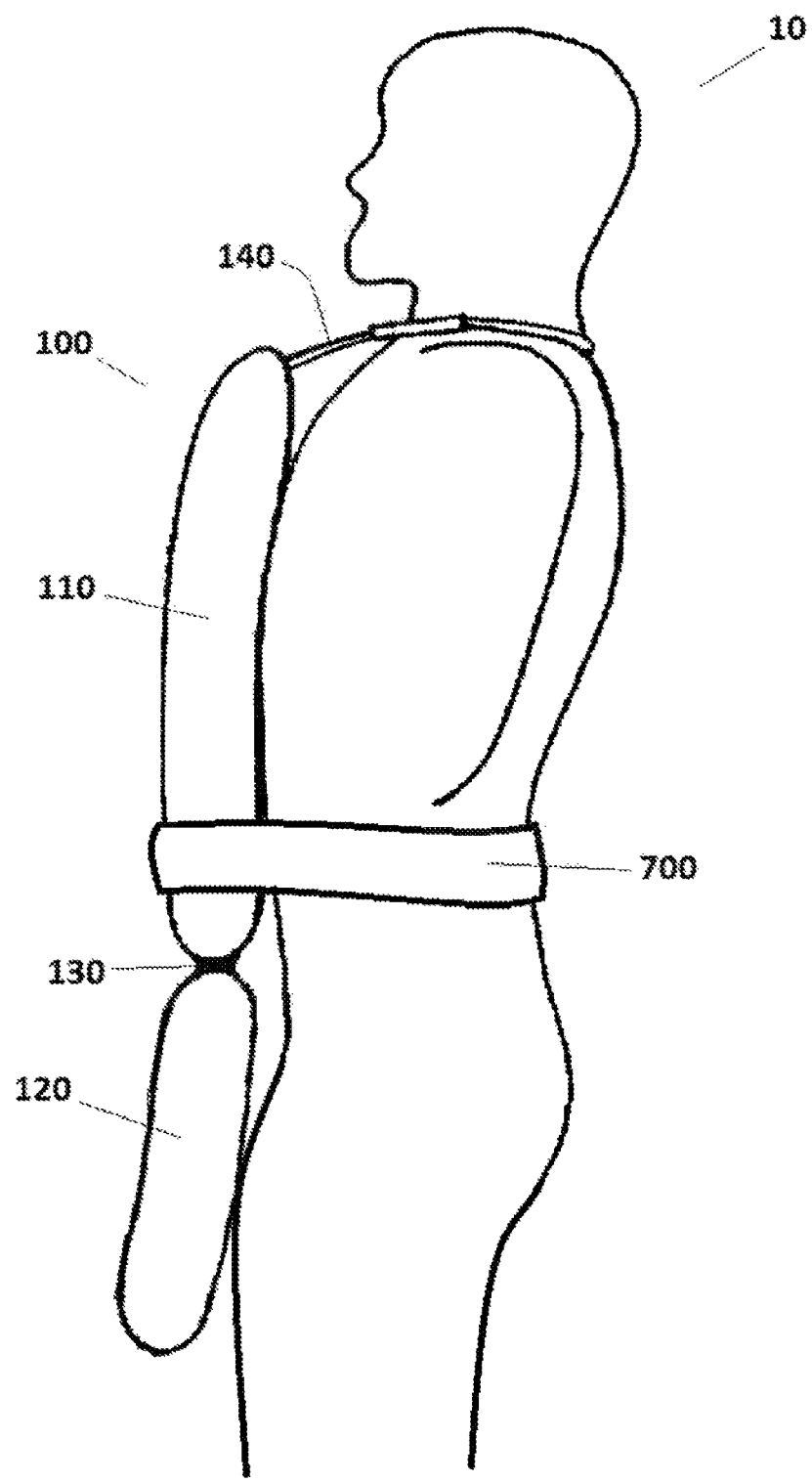
FIG. 1 is a side elevation view of a user wearing an example body-mountable cushion structure for post-surgical support and protection according to various example embodiments, depicting the user in a non-sitting position, such as in the standing position or lying in a prone or supine position.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of certain example embodiments. Particular example embodiments may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of any methods shown and described herein are not necessarily performed in the order indicated, or performed at all in certain embodiments. Accordingly, some implementations of methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

Turning to FIGS. 1-7, provided in various example embodiments is a body-mountable cushion structure for post-surgical support and protection, comprising an elongated planar resilient cushion structure 100, comprising an upper pillow 110 pivotably connected with a lower pillow 120, that may be adapted to support and provide protection for any or all of the chest, abdomen, torso, and upper legs of a user 10 from automotive seat belts and the like, and to address the support, comfort, therapeutic, and protection needs of a post-surgical patient 10, in a manner improved from that shown or described in the art such as Huggins and Benedick, which are incorporated herein. For example, in prior devices designed for the present purposes the user 10 would not be well protected, if protected at all, from the lap belt portion of an automotive seatbelt, without the additional complexity and difficulty of perhaps attaching the seatbelt to the cushion so that it does not slide down onto the user's lap. In addition to protecting the user's chest area, in various example embodiments the present cushion structure 100 protects the user's lap area from the lap belt portion of an automotive seatbelt without having to attach the seatbelt to the structure 100. Additionally, the cushion structure 100 may be provided with one or more pockets 620, 630 for removably containing one or more ice packs, vacuum pumps, other medical devices, and other items for therapeutic treatment of the user. It is understood that any number of pockets 620, 630, or other pockets, including optionally no pockets at all, may be provided in any suitable location on either or both sides of cushion structure 100, on either the upper or lower pillow portions 110, 120.

Figure 2:
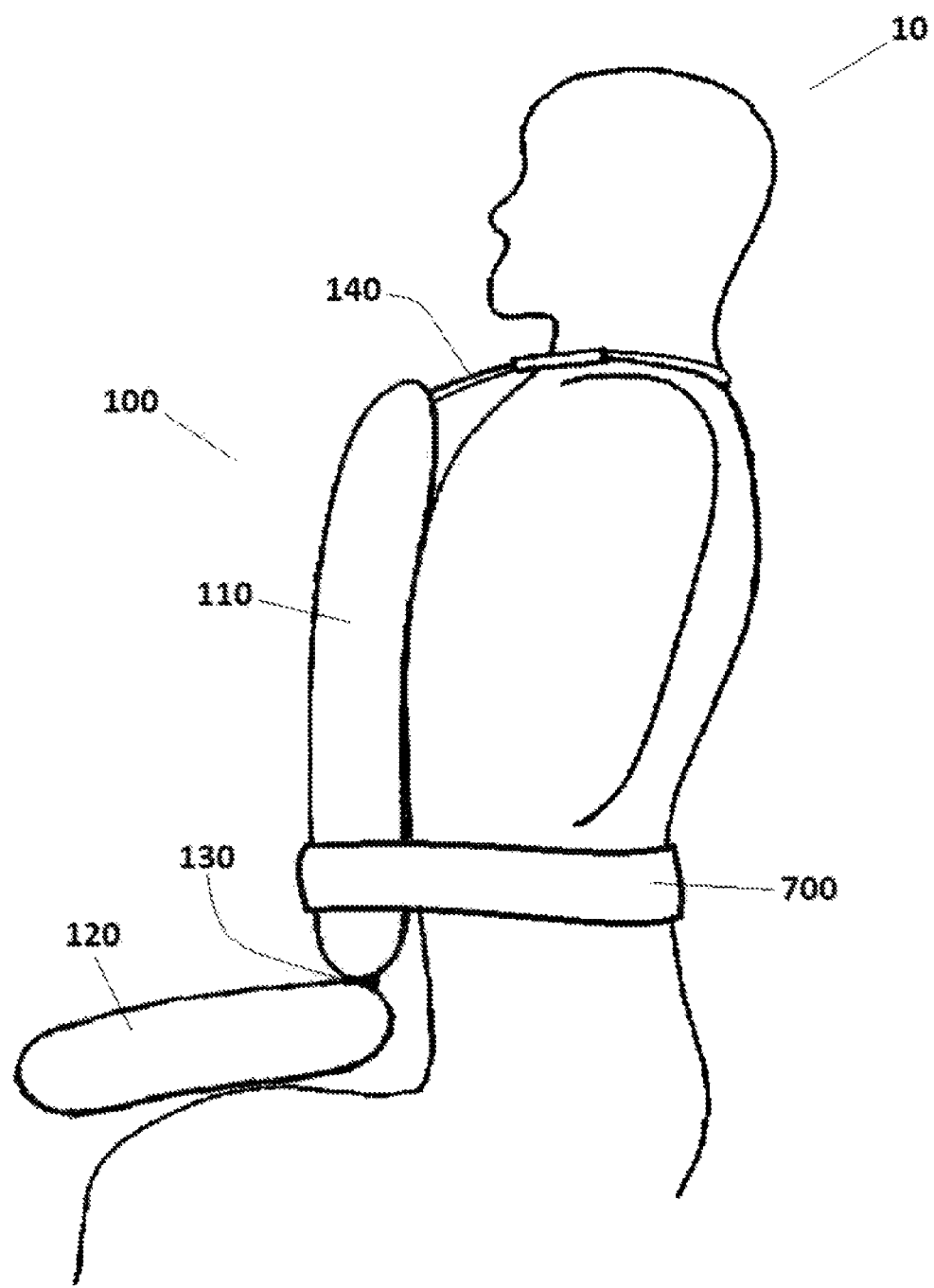
FIG. 2 is a side elevation view of a user wearing the example body-mountable cushion structure for post-surgical support and protection of FIG. 1, depicting the user in a sitting position.

In various example embodiments as shown in FIGS. 1 and 2, the patient 10 may wear the cushion structure 100 with an adjustable length and resilient strap 700, such as an elastic belt binder, for example, binding the cushion structure 100 to the patient's chest or abdominal area. The patient or user 10 may wear the cushion structure 100 in a car, truck, bus, or other vehicle when discharged from a hospital, for example. The cushion structure 100 may cover both the chest and abdominal areas with ice-packs (not shown) placed inside pockets 620, 630, positioned proximate the patient's sites of surgery. The cushion structure 100 may be sized, shaped, and constructed to support, protect, and cushion the patient's surgical incisions, drains, wounds, dressings, and any other indicated procedures when wearing a seatbelt for the duration of their ride home, for example. The cushion structure 100 may provide comfort when wearing a seatbelt by absorbing the seatbelt's pressure so it does not rub into the surgical sites. The seat belt pressure could potentially be harmful and alter the surgical sites during sudden stops or during an automobile collision. The cushion structure 100 may also be used for therapeutic purposes by placing ice-packs inside one or more pockets 620, 630, or otherwise, to reduce swelling and bleeding during both travel, and extended home use of the cushion structure 100. The cushion structure 100 may comprise one or more elastic or otherwise resilient and adjustable length and resilient strap 700, such as an elastic belt binder, that wraps around the chest or abdominal areas (or both) of the cushion structure 100 to function as a binder to bind the cushion structure 100 to the patient 10. The adjustable length and resilient strap 700, such as an elastic belt binder, provides more support and comfort for the patient 10, and helps keep the cushion structure 100 in position during entry and exit from a vehicle, for example. The cushioned cushion structure 100 is readily bendable, for instance at the waist as shown in FIG. 2. This may be accomplished in certain example embodiments by providing two planar pieces of cushioning foam 310, 320 (FIG. 3), separated by a foldable region 130, such as a seam. Combining ice packs inside one or more pockets 620, 630, and an adjustable length and resilient strap 700, such as an elastic belt binder, with the disclosed structure 100 helps the patient 10 cough, sneeze, or to bear down while pushing the cushion structure 100 onto the chest or abdominal area of the patient 10. This action helps reinforce or splint together incisions in the patient 10. In various example embodiments the cushion structure 100 may have multiple uses: it may support, protect, cushion, comfort, and cool with ice packs or similar heating or cooling devices, regardless whether they actually contain ice (herein broadly referred to as "ice packs"). For example, a surgeon may recommend the cushion structure 100 for a patient 10 who had breast reconstruction surgery, heart surgery, cesarean section, any type of laparoscopic procedure, and any type of plastic surgery that involved the chest or abdominal area. It may be adapted to last for travel and extended home use as long as the patient 10 needs, depending on the progress of their postoperative recovery phase. The patient 10 may continue using the cushion structure 100 for follow-up doctor's appointments, daily travel, and home use per physician's recommendations.

Characteristics of the cushion structure 100 in various example embodiments may optionally include a substantially rectangular one-piece design as best shown in FIGS. 4 and 6, constructed to cover the chest and abdominal area of the patient, an adjustable head or neck strap 140, utilitarian fabric construction surrounding a high-density foam core 310, 320 (FIG. 3), resistance to soiling, multiple pockets 610, 630, or otherwise, one or more adjustable length and resilient straps 700, such as an elastic belt binder, and a variety of sizes configured to protect the torso of a variety of users, for example as shown in FIGS. 1 and 2 (for instance, extending from mid-thigh to upper chest).

Various example materials, dimensions, and other details are provided in U.S. provisional patent application Ser. No. 62/599,687, all of which is incorporated herein by reference. Additionally and by way of further non-limiting example, the outer fabric used for the structure 100 may comprise any suitable fabric(s), such as any nylon fabric, whether or not rip-stop fabric, and the first and second flexible and resilient cushions 310, 320 may be formed from high density foam or polyurethane foam, for example, which may be one inch thick, or between three-quarters of an inch thick and two inches thick, for example, or any suitable thickness.

The example shown in FIGS. 1-7 will now be described in detail. Provided in various example embodiments is a cushion structure 100 for a post-surgical patient 10 to wear, comprising: an upper pillow portion 110, comprising: a first flexible and resilient cushion 310 having a first thickness between sides 111 and 113, a first width between sides 116 and 118, and a first height between top area 112 and bottom area 114, the first width and first height being perpendicular to the first thickness and to each other, the first width and first height approximating upper body width and rib cage height dimensions of a patient 10, for instance using dimensions as shown in U.S. provisional patent application Ser. No. 62/599,687, or any other suitable dimensions. A first fabric cover portion at least substantially surrounds and encloses the first flexible and resilient cushion 310, as depicted by opening 117 in the first fabric cover that can be opened and shut with a fastener such as hook and loop fasteners 119, for example.

Also provided is a lower pillow portion 120, comprising: a second flexible and resilient cushion 320 having a second thickness between sides 121 and 123, a second width between sides 126 and 128, and a second height between top area 122 and bottom area 124, the second width and second height being perpendicular to the second thickness and to each other, the second width between sides 126 and 128 being at least approximately the same as the first width between sides 116 and 118, and the second height between top area 122 and bottom area 124, being less than the first height between top area 112 and bottom area 114, for instance using dimensions as shown in U.S. provisional patent application Ser. No. 62/599,687, or any other suitable dimensions. A second fabric cover portion at least substantially surrounds and encloses the second flexible and resilient cushion 320, as depicted by opening 127 in the second fabric cover that can be opened and shut with a fastener such as hook and loop fasteners 129, for example.

The upper part 122 of the lower pillow portion 120 may be flexibly connected with a lower part 114 of the upper pillow portion 110 so that the lower pillow portion 120 can readily pivot with respect to the upper pillow portion 110, for instance between the positions shown in FIGS. 1 and 2. This can be accomplished in any suitable manner, for instance by providing a foldable region 130, such as a seam. For example, the first and second fabric cover portions can be formed from one or more single pieces of fabric that extend from the upper pillow portion 110 to the lower pillow portion 120, through which a seam is sewn at foldable region 130. Additionally or alternatively, the first and second flexible and resilient cushions 310, 320 may be formed from a single cushion that is notched, thinned, or otherwise made pivotably flexible at foldable region 130.

One or more straps 140 may be configured to engage the upper pillow portion 110 and an upper body area of the patient 100 (FIGS. 1 and 2) to removably hold the upper pillow portion 110 of the cushion structure proximate a chest area of the patient 10, for instance as shown in FIGS. 1 and 2. One or more straps 140 may comprise thirty-six inch long one-inch wide nylon strap or polypropylene belting, for example. One or more adjustment and/or disconnect means 145 may be provided in strap 140, such as a double-ring buckle, or a side release buckle, also sometimes known as a break-away buckle or parachute buckle.

In various example embodiments the cushion structure 100 may further comprise a patient-facing first side 113, 123, and a second side 111, 121, opposite the first side 113, 123, and the upper pillow portion 110 may comprise one or more first pockets 610, 620 located on the upper pillow portion 110 on the patient-facing first side 113, each of the one or more first pockets 610, 620 oriented and configured to removably receive therein an ice pack (as depicted in at least one of the figures in U.S. provisional patent application Ser. No. 62/599,687, all of which is incorporated herein by reference). The one or more ice packs may be hospital standard-issue white pouch with strings 6.5 inch by 14 inch, for example. The apparatus can be configured to hold gel ice packs too. Any such devices may be used, and are considered "ice packs". An entire ice pack need not fit entirely within pocket 610 or 620 to be considered being within pockets 610 or 620. The cushion structure 100 may be designed to position the ice pack(s) in the pockets 610, 620 proximate a body area of the patient 10, such as an incision area, for example, when the cushion structure 100 is worn by the patient 10, for instance as depicted in FIGS. 1 and 2. In various example embodiments, pockets 610, 620 can be opened and shut with fasteners such as hook and loop fasteners 611, 621, for example, as depicted in FIG. 6. In alternative embodiments, one or more pockets 610, 620 can also or alternatively be placed on the second side 111 opposite the patient-facing first side 113.

In various example embodiments the cushion structure 100 may further comprise one or more second pockets 630 located on the upper and/or lower pillow portions 110, 120 on the patient-facing first side 113, 123, or on the second side 11, 121 opposite the patient-facing first side 113, 123, or both on the patient-facing first side 113, 123 and on the second side 111, 121, wherein at least one of the one or more second pockets 630 may oriented and configured to removably receive therein either one or more ice packs, or to inconspicuously hold a typical negative-pressure wound therapy vacuum pump of the type known in the medical field (not shown), such as those manufactured by Devon Medical Products, for example. In various example embodiments, second pockets 630 can be opened and shut with fasteners such as hook and loop fasteners 631, for example, as depicted in FIG. 6. To avoid prolixity, separate figures are not provided showing all possible combinations and permutations of placement of pockets 610, 620, 630, as they are sufficiently described herein as any number of each type of pocket 610, 620, 630, including optionally no pockets at all, can be located on either the patient-facing first side 113, 123, and on the second side 111, 121, opposite the patient-facing first side 113, 123, on the upper pillow portion 110 and/or the lower pillow portion 120. In various example embodiments, second pockets 630 may extend all the way from a first side 116 or 126 to a second side 118 or 128 of the cushion structure 100. In various example embodiments no second pockets 630 may be provided on the cushion structure 100.

As depicted in FIG. 3, in various example embodiments the cushion structure 100 may comprise the first fabric cover portion comprising a first selectably openable access area 117 located and sized so that the first flexible and resilient cushion 310 can be removed and replaced through the first selectably openable access area 117. In various example embodiments the cushion structure 100 may further comprise the second fabric cover portion comprising a second selectably openable access area 127 located and sized so that the second flexible and resilient cushion 320 can be removed and replaced through the second selectably openable access area 127. Alternatively, areas 117, 127 may be sewn shut so that the cushion(s) 310, 320 cannot be removed from the fabric covering.

Figure 7:
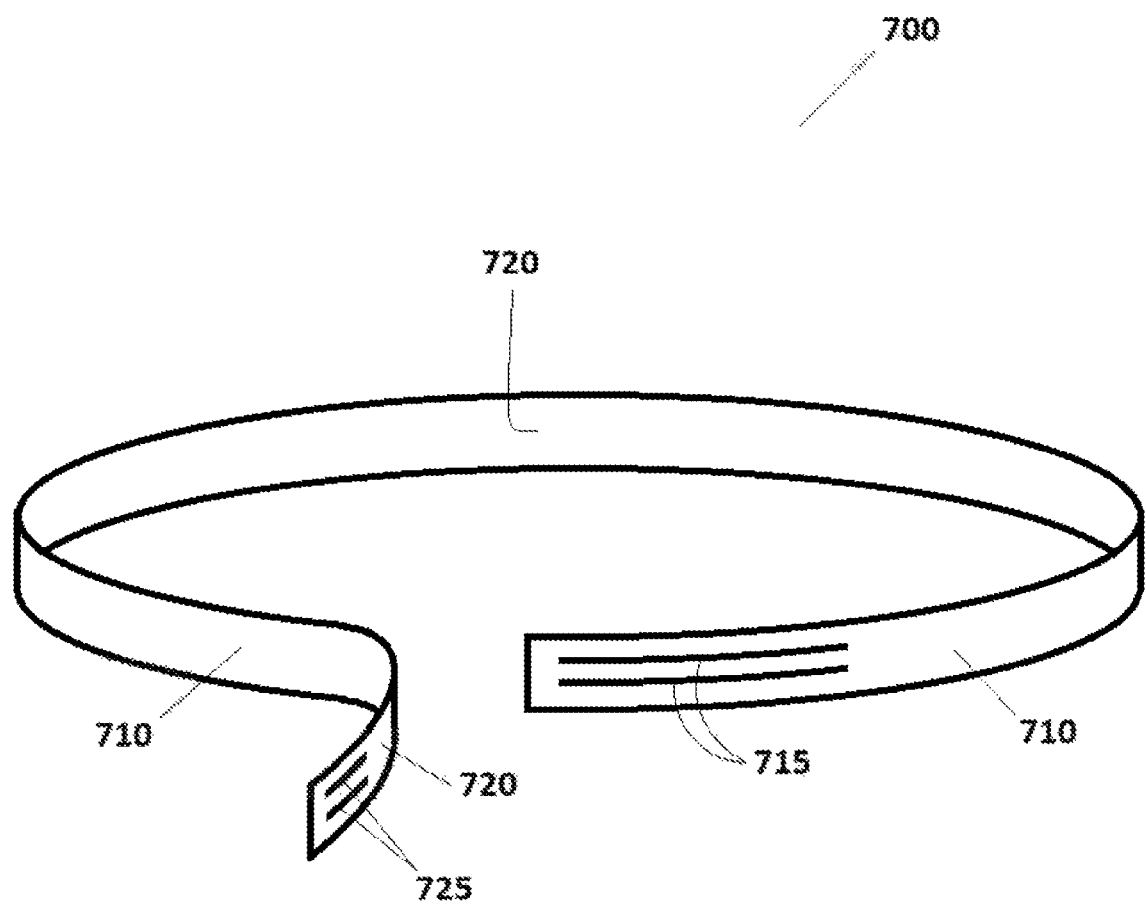
FIG. 7 is top perspective view of an example adjustable length and resilient strap, such as an elastic belt binder, configured for optional use with various example embodiments of body-mountable cushion structures for post-surgical support and protection.

As best shown in FIG. 4, in various example embodiments the cushion structure 100 may further comprise a first adjustable length strap 140 attached at a first end to a first location on an upper part 112 of the upper pillow portion 110 and attached at a second end to a second location on the upper part 112 of the upper pillow portion 110, the first adjustable length strap 140 configured to extend around, and be supported at least in part by, a neck area of the patient 10 when the cushion structure 100 is worn by the patient 10, for example as shown in FIGS. 1 and 2. As shown in FIGS. 1, 2, and 7, in various example embodiments the cushion structure 100 may further comprise an adjustable length and resilient strap 700, such as an elastic belt binder, configured to extend around, and be supported at least in part by, the upper pillow portion 110 and a back area of the patient 10 when the cushion structure 100 is worn by the patient 10. The adjustable length and resilient strap 700, such as an elastic belt binder, may comprise a relatively wide elastic strap, such as about three inches wide, for example, of appropriate length having complimentary hook and loop fastener material, 715, 725, affixed to outer and inner surfaces, 710, 720, respectively, of the ends of strap 700 as shown in FIG. 7. As used herein the term "adjustable length" is meant in the same way that a belt for one's pants is adjustable length, i.e., while the overall length of such a belt remains the same, one of its ends can be hooked to the other end of the belt at different points to give it effectively different lengths to fit larger or smaller waist sizes, for example. Thus, in a similar way here, "adjustable length" means adjustable effective length when used as a strap or belt as shown and described herein. In various example embodiments the adjustable length and resilient strap 700 may or may not be attached to the upper pillow portion 110 (shown unattached).

Also provided in various example embodiments is a method of using a cushion structure, comprising the steps of: providing a cushion structure 100 as described herein for a post-surgical patient 10 to wear, and removably engaging the upper pillow portion 110 with an upper body area (FIGS. 1, 2) of the patient 10 with the one or more straps 140, 700, so that the upper pillow portion 110 is proximate a chest area of the patient 10. In various example embodiments the method of using a cushion structure 100 may further comprise the steps of removably engaging the upper pillow portion 110 with an upper body area of the patient 10 with the one or more straps 140, 700, so that the lower pillow portion 120 is proximate either a lower abdomen area of the patient 10, or an upper leg area of the patient 10, or both (see FIG. 2), when the upper pillow portion 110 is proximate a chest area of the patient 10.

With continuing reference to FIGS. 1 and 2, in various example embodiments the method of using a cushion structure 100 may further comprise the steps of the patient 10 moving between a standing position (FIG. 1) and a sitting position (FIG. 2) and moving an upper leg area of the patient 10 relative to the chest area of the patient 10, the movement of the upper leg area of the patient causing the lower pillow portion 120 to pivot with respect to the upper pillow portion 110 about the foldable region 130. In various example embodiments the steps of moving an upper leg area of the patient 10 relative to the chest area of the patient 10 and causing the lower pillow portion 120 to pivot with respect to the upper pillow portion 110, may further comprise the steps of: the patient 10 moving between a first position outside of a vehicle (as in FIG. 1) and a second position seated inside a vehicle (as in FIG. 2) while wearing a vehicle seatbelt over the cushion structure 100, for instance as described in Huggins and Benedick and as shown in at least one of the figures in U.S. provisional patent application Ser. No. 62/599,687, all of which is incorporated herein by reference.

Further provided in various example embodiments is a method of using a cushion structure 100, comprising the steps of: providing a cushion structure 100 as described herein for a post-surgical patient 10 to wear; placing at least one ice pack (shown in at least one of the figures in U.S. provisional patent application Ser. No. 62/599,687) in the one or more first pockets 610, 620; removably engaging the upper pillow portion 110 with an upper body area of the patient 10 with the one or more straps 140, 700 so that the upper pillow portion 110 is proximate a chest area of the patient 10 and the one or more ice packs are proximate a body area of the patient 10, and so the lower pillow portion 120 is proximate either a lower abdomen area of the patient 10, or an upper leg area of the patient 10, or both (see, e.g., FIG. 2); the patient 10 moving between a standing position (FIG. 1) and a sitting position (FIG. 2) and moving an upper leg area of the patient 10 relative to the chest area of the patient 10, the movement of the upper leg area of the patient 10 causing the lower pillow portion 120 to pivot with respect to the upper pillow portion 110 about the foldable region 130; and the patient 10 moving between a first position outside of a vehicle (FIG. 1) and a second position seated inside a vehicle (FIG. 2) while wearing a vehicle seatbelt over the cushion structure 100, for instance as described in Huggins and Benedick and as shown in at least one of the figures in U.S. provisional patent application Ser. No. 62/599,687, all of which is incorporated herein by reference Multiple sets of example dimensional drawings are provided in U.S. provisional patent application Ser. No. 62/599,687 to demonstrate example alternative designs. Many other designs are possible within the scope of the intended invention. The materials of the apparatus are not limited to the shown size, color, and shape; other designs are contemplated that provide the same improved functionality.

It will be recognized that numerous different features or components may be presented in the embodiments shown and described herein, and that no one embodiment may be specifically shown and described as including all such features and components. Accordingly, it is understood that the subject matter of the present disclosure may be intended to encompass any and all combinations of the different features and components that may be shown and described herein, and, without limitation, that any suitable arrangement of features and components, in any combination, may be used. Thus, it is distinctly understood that claims directed to any such combination of features or components, whether or not specifically embodied herein, may be intended to find support in the present disclosure.

Thus, while the subject matter of the present disclosure has been described with reference to the foregoing embodiments and considerable emphasis has been placed herein on the structures and structural interrelationships between the component parts of the embodiments disclosed, it will be appreciated that other embodiments may be made and that many changes may be made in the embodiments illustrated and described without departing from the principles hereof. Obviously, modifications and alterations will occur to others upon reading and understanding the preceding detailed description. Accordingly, it is distinctly understood that the foregoing descriptive matter should be interpreted merely as illustrative of the subject matter of the present disclosure and not as a limitation. As such, it is intended that the subject matter of the present disclosure be construed as including all such modifications and alterations.

The invention claimed is:

1. A cushion structure for a post-surgical patient to wear, comprising:
    an upper pillow portion, comprising a first flexible and resilient cushion having a first width and a first height approximating upper body width and rib cage height dimensions of a patient;
    a lower pillow portion, comprising a second flexible and resilient cushion having a second width and a second height, the second width being at least approximately the same as the first width and the second height being less than the first height, the lower pillow portion pivotally coupled to the upper pillow portion;
    a strap configured to engage the upper pillow portion and an upper body area of the patient to removably hold the upper pillow portion of the cushion structure proximate a chest area of the patient; and
    wherein the upper pillow portion comprises one or more first pockets located on the upper pillow portion on a patient-facing first side, each of the one or more first pockets oriented and configured to receive an ice pack and to position the ice pack proximate a body area of the patient.

2. The cushion structure of claim 1, wherein the lower pillow portion comprises one or more second pockets located on the patient-facing first side, at least one of the one or more second pockets oriented and configured to receive a negative-pressure wound therapy vacuum pump.

3. The cushion structure of claim 1, wherein the lower pillow portion comprises one or more second pockets located on a second side opposite a patient-facing first side, at least one of the one or more second pockets oriented and configured to receive therein a negative-pressure wound therapy vacuum pump.

4. The cushion structure of claim 1, further comprising:
an ice pack within at least one of the one or more first pockets.

5. The cushion structure of claim 1, further comprising:
an ice pack within each of the one or more first pockets.

6. The cushion structure of claim 2, further comprising:
a negative-pressure wound therapy vacuum pump within one of the one or more second pockets.

7. The cushion structure of claim 3, further comprising:
a negative-pressure wound therapy vacuum pump within one of the one or more second pockets.

8. The cushion structure of claim 2, further comprising:
an ice pack within at least one of the one or more first pockets; and
a negative-pressure wound therapy vacuum pump within one of the one or more second pockets.

9. The cushion structure of claim 3, further comprising:
an ice pack within at least one of the one or more first pockets; and
a negative-pressure wound therapy vacuum pump within one of the one or more second pockets.

10. The cushion structure of claim 1, further comprising:
a first fabric cover portion at least substantially surrounding and enclosing the first flexible and resilient cushion; and
a second fabric cover portion at least substantially surrounding and enclosing the second flexible and resilient cushion.

11. The cushion structure of claim 10, wherein the first fabric cover portion comprises a selectably openable access area located and sized so that the first flexible and resilient cushion can be removed and replaced through the selectably openable access area.

12. The cushion structure of claim 11, wherein the second fabric cover portion comprises a selectably openable access area located and sized so that the second flexible and resilient cushion can be removed and replaced through the selectably openable access area.

13. The cushion structure of claim 10, wherein the first fabric cover portion comprises a first selectably openable access area located and sized so that the first flexible and resilient cushion can be removed and replaced through the first selectably openable access area, and wherein the second fabric cover portion comprises a second selectably openable access area located and sized so that the second flexible and resilient cushion can be removed and replaced through the second selectably openable access area.

14. The cushion structure of claim 1, wherein the strap has an adjustable length and is resiliently elastic and configured to extend around, and be supported at least in part by, the upper pillow portion and a back area of the patient.

15. A method of using a cushion structure, comprising the steps of:
providing a cushion structure according to claim 1 for a post-surgical patient to wear; and
engaging the upper pillow portion with an upper body area of the patient with the strap so that the upper pillow portion is proximate a chest area of the patient.

16. The method of claim 15, wherein the step of engaging the upper pillow portion further comprises positioning the lower pillow portion proximate either a lower abdomen area of the patient, or an upper leg area of the patient, or both.

17. The method of claim 15, further comprising the steps of:
the patient moving between a standing position and a sitting position and moving an upper leg area of the patient relative to the chest area of the patient, the movement of the upper leg area of the patient causing the lower pillow portion to pivot with respect to the upper pillow portion.

18. The method of claim 17, wherein the step of moving the upper leg area relative to the chest area is performed while the patient is moving between a first position outside of a vehicle and a second position seated inside the vehicle and wearing a vehicle seatbelt over the cushion structure.

19. A method of using a cushion structure, comprising the steps of:
providing a cushion structure according to claim 1 for a post-surgical patient to wear;
placing at least one ice pack in the one or more first pockets;
removably engaging the upper pillow portion with an upper body area of the patient with the strap so that the upper pillow portion is proximate a chest area of the patient and so that the one or more ice packs are proximate a body area of the patient and so that the lower pillow portion is proximate either a lower abdomen area of the patient, or an upper leg area of the patient, or both;
the patient moving between a standing position and a sitting position and moving an upper leg area of the patient relative to the chest area of the patient, the movement of the upper leg area of the patient causing the lower pillow portion to pivot with respect to the upper pillow portion; and
the patient moving between a first position outside of a vehicle and a second position seated inside the vehicle while wearing a vehicle seatbelt over the cushion structure.

* * * * *